US008580230B2

(12) United States Patent
Huang et al.

(10) Patent No.: US 8,580,230 B2
(45) Date of Patent: Nov. 12, 2013

(54) MATERIALS AND METHODS FOR MRI CONTRAST AGENTS AND DRUG DELIVERY

(75) Inventors: Songping D. Huang, Kent, OH (US); Soumitra Basu, Kent, OH (US); Anatoly K. Khitrin, Kent, OH (US); Mohammadreza Shokouhimehr, Kent, OH (US); Eric Scott Soehnlen, Kent, OH (US)

(73) Assignee: Kent State University, Kent, OH (US)

( * ) Notice: Subject to any disclaimer, the term of this patent is extended or adjusted under 35 U.S.C. 154(b) by 519 days.

(21) Appl. No.: 12/710,633

(22) Filed: Feb. 23, 2010

(65) Prior Publication Data

US 2010/0215587 A1 Aug. 26, 2010

(51) Int. Cl.
*A61B 5/055* (2006.01)
*A61K 51/00* (2006.01)
*A61K 49/00* (2006.01)

(52) U.S. Cl.
USPC .......... 424/9.36; 424/9.32; 424/1.11; 424/9.1

(58) Field of Classification Search
USPC ................................ 424/9.36, 1.11, 9.1, 9.32
See application file for complete search history.

(56) References Cited

U.S. PATENT DOCUMENTS

| | | | |
|---|---|---|---|
| 3,904,737 A | 9/1975 | Paris et al. | |
| 4,951,675 A | 8/1990 | Groman et al. | |
| 5,219,554 A | 6/1993 | Groman et al. | |
| 5,336,762 A | 8/1994 | Ranney | |
| 5,492,814 A | 2/1996 | Weissleder | |
| 5,565,215 A | 10/1996 | Gref et al. | |
| 5,707,604 A | 1/1998 | Ranney | |
| 6,106,866 A | 8/2000 | Ranney | |
| 6,139,819 A | 10/2000 | Unger et al. | |
| 6,368,574 B1 | 4/2002 | Akeson et al. | |
| 7,235,227 B2 | 6/2007 | Lanza et al. | |
| 7,354,568 B1 | 4/2008 | Meade et al. | |
| 7,393,924 B2 | 7/2008 | Vitaliano et al. | |
| 7,396,589 B2 | 7/2008 | Cho et al. | |
| 7,407,646 B2 | 8/2008 | Laurent et al. | |
| 7,419,654 B2 | 9/2008 | Dewanjee | |
| 7,452,551 B1 | 11/2008 | Unger et al. | |
| 7,459,145 B2 | 12/2008 | Bao et al. | |
| 7,682,613 B2 | 3/2010 | Fabene et al. | |
| 8,092,783 B2 * | 1/2012 | Huang et al. | 424/9.36 |
| 2002/0165349 A1 | 11/2002 | Kirsch et al. | |
| 2005/0260669 A1 | 11/2005 | Kirsch et al. | |
| 2006/0014019 A1 * | 1/2006 | Kuebelbeck et al. | 428/403 |
| 2006/0025713 A1 | 2/2006 | Rosengart et al. | |
| 2006/0093555 A1 | 5/2006 | Torres et al. | |
| 2007/0009931 A1 | 1/2007 | Kirsch | |
| 2007/0053839 A1 | 3/2007 | Zhang | |
| 2007/0135393 A1 | 6/2007 | Monje et al. | |
| 2007/0258907 A1 | 11/2007 | Davis | |
| 2008/0118440 A1 | 5/2008 | Liu et al. | |
| 2008/0154128 A1 | 6/2008 | Milner | |
| 2008/0284427 A1 | 11/2008 | van Zijl et al. | |
| 2009/0211494 A1 | 8/2009 | Kawamoto et al. | |
| 2010/0215587 A1 | 8/2010 | Huang et al. | |
| 2010/0254912 A1 | 10/2010 | Huang et al. | |

FOREIGN PATENT DOCUMENTS

| | | | |
|---|---|---|---|
| EP | 1902734 | | 3/2008 |
| JP | 2006083054 | | 3/2006 |
| JP | 2008046001 | * | 2/2008 |
| JP | 2008046001 | A | 2/2008 |
| WO | 0071169 | | 11/2000 |
| WO | 02100269 | | 12/2002 |
| WO | 2006086343 | | 8/2006 |
| WO | 2006093555 | | 9/2006 |
| WO | 2006119102 | | 11/2006 |
| WO | 2007021621 | | 2/2007 |
| WO | 2007095871 | | 8/2007 |
| WO | 2007106683 | | 9/2007 |
| WO | 2007127231 | | 11/2007 |
| WO | 2007140617 | | 12/2007 |
| WO | 2008054523 | | 5/2008 |
| WO | 2008081923 | | 7/2008 |

OTHER PUBLICATIONS

Of Itaya et al. ("Spectroelectrochemistry and Electrochemical Preparation Method of Prussian Blue Modified Electrodes" in J. Am. Chem. Soc. 1982, 104, 4767-4772).*
Corot, C.; Robert, P.; Idee, J. M.; Port, M., Recent advances in iron oxide nanocrystal technology for medical imaging. Advanced Drug Delivery Reviews 2006, 58 (14), 1471-1504.
Di Marco, M.; Sadun, C.; Port, M.; Guilbert, I.; Couvreur, P.; Dubernet, C., Physicochemical characterization of ultrasmall superparamagnetic iron oxide particles (USPIO) for biomedical application as MRI contrast agents. International Journal of Nanomedicine 2007, 2 (4), 609-622.
Duguet, E.; Vasseur, S.; Mornet, S.; Devoisselle, J. M., Magnetic nanoparticles and their applications in medicine. Nanomedicine 2006, 1 (2), 157-168.
Laurent, S.; Forge, D.; Port, M.; Roch, A.; Robic, C.; Elst, L. V.;

(Continued)

*Primary Examiner* — Blessing Fubara
(74) *Attorney, Agent, or Firm* — Hahn Loeser + Parks LLP; Scott M. Oldham, Esq.

(57) ABSTRACT

A material useful as a MRI contrast agent used for medical imaging, drug delivery platform or other functions are provided as a class of non-gadolinium and non-iron oxide based materials that comprise Prussian blue materials or analogue materials. The materials may be used as $T_1$-weighted and/or $T_2$-weighted MRI contrast agents for imaging, including cellular imaging, in clinical diagnosis and biomedical research applications. The agent is a compound created from Prussian blue materials that is non-toxic, and can be internalized by cells through endocytosis. The Prussian blue materials may also be used for drug delivery applications. The Prussian blue materials may be administered orally to a subject in either medical imaging or drug delivery applications or dual modality MRI-Fluorescence imaging agent.

30 Claims, 2 Drawing Sheets

(56) References Cited

OTHER PUBLICATIONS

Muller, R. N., Magnetic iron oxide nanoparticles: Synthesis, stabilization, vectorization, physicochemical characterizations, and biological applications. Chemical Reviews 2008, 108 (6), 2064-2110.
Muller, R. N.; Vander Elst, L.; Roch, A.; Peters, J. A.; Csajbok, E.; Gillis, P.; Gossuin, Y., Relaxation by metal-containing nanosystems. In Advances in Inorganic Chemistry—Including Bioinorganic Studies, vol. 57, 2005; vol. 57, pp. 239-292.
Tombach, B.; Reimer, P., Soluble paramagnetic chelates and iron oxides as contrast agents for stabilized colloidal particle solutions of magnetic resonance imaging. Current Medicinal Chemistry 2005, 12 (23), 2795-2804.
Dominguez-Vera, J. M.; Colacio, E., Nanoparticles of Prussian blue ferritin: A new route for obtaining nanomaterials. Inorganic Chemistry 2003, 42 (22), 6983-6985.
Fornasieri, G.; Bleuzen, A., Controlled synthesis of photomagnetic nanoparticles of a Prussian Blue analogue in a silica xerogel. Angewandte Chemie-International Edition 2008, 47 (40), 7750-7752.
Uemura, T.; Kitagawa, S., Prussian blue nanoparticles protected by poly(vinylpyrrolidone). Journal of the American Chemical Society 2003, 125 (26), 7814-7815.
Vaucher, S.; Li, M.; Mann, S., Synthesis of Prussian blue nanoparticles and nanocrystal superlattices in reverse microemulsions. Angewandte Chemie-International Edition 2000, 39 (10), 1793-1796.
Caravan P et al. "Gadolinium(III) Chelates as MRI Contrast Agents: Structure, Dynamics, and Applications" Chemical Reviews pp. 2293-2352, 1999.
Allen, M. J.; Meade, T. J., "Magnetic resonance contrast agents for medical and molecular imaging". In Metal Ions in Biolgical Systems, vol. 42: Metal Complexes in Tumor Diagnosis and as Anticancer Agents, 2004; vol. 42, pp. 1-38.
Hermann, P.; Kotek, J.; Kubicek, V.; Lukes, I., "Gadolinium(III) complexes as MRI contrast agents: ligand design and properties of the complexes". Dalton Transactions 2008, (23), 3027-3047.
Bjornerud, A.; Johansson, L., The utility of superparamagnetic contrast agents in MRI: theoretical consideration and applications in the cardiovascular system. NMR in Biomedicine 2004, 17 (7), 465-477.
Aime, S.; Botta, M.; Terreno, E., "Gd(III)-based contrast agents for MRI". In Advances in Inorganic Chemistry—Including Bioinorganic Studies, vol. 57, 2005; vol. 57, pp. 173-237.
Aime, S.; Crich, S. G.; Gianolio, E.; Giovenzana, G. B.; Tei, L.; Terreno, E., "High sensitivity lanthanide(III) based probes for MR-medical imaging". Coordination Chemistry Reviews 2006, 250 (11-12), 1562-1579.
Bianchi, A.; Calabi, L.; Corana, F.; Fontana, S.; Losi, P.; Maiocchi, A.; Paleari, L.; Valtancoli, B., "Thermodynamic and structural properties of Gd(III) complexes with polyamino-polycarboxylic ligands: basic compounds for the development of MRI contrast agents". Coordination Chemistry Reviews 2000, 204, 309-393.
Caravan, P., "Strategies for increasing the sensitivity of gadolinium based MRI contrast agents". Chemical Society Reviews 2006, 35 (6), 512-523.
Chan, K. W. Y.; Wong, W. T., Small molecular gadolinium(III) complexes as MRI contrast agents for diagnostic imaging. Coordination Chemistry Reviews 2007, 251 (17-20), 2428-2451.
Ferlay, S.; Mallah, T.; Ouahes, R.; Veillet, P.; Verdaguer, M., "A room-temperature organometallic magnet based on prussian blue". Nature 1995, 378 (6558), 701-703.
Arbab, A. S.; Liu, W.; Frank, J. A., "Cellular magnetic resonance imaging: current status and future prospects". Expert Review of Medical Devices 2006, 3 (4), 427-439.
Gries, H., "Extracellular MRI contrast agents based on gadolinium". In Contrast Agents I, 2002; vol. 221, pp. 1-24.
Arbab, A. S.; Frank, J. A., "Cellular MRI and its role in stem cell therapy". Regenerative Medicine 2008, 3 (2), 199-215.
Keggin, J. F.; Miles, F. D. Nature 1936, 97, 577-578.
Robin, M. B.; Day, P. Adv. Inorg. Chem. Radiochem. 1967, 10, 247 et seq.
Ludi, A.; Glüdel, H. U. Structure and Bonding 1973, 14, 1-22.
Buser, H. J.; Schwarzenbach, D.; Petter, W.; Ludi, A. Inorg. Chem. 1977, 16, 2704-2710.
Dunbar, K. R.; Heintz, R. A. Prog. Inorg. Chem. 1997, 45, 283-391.
Ferlay, S.; Mallah, T.; Ouahés, R.; Veillet, P.; Verdaguer, M. Nature 1995, 378, 701-703. (b) Entley, W. R.; Girolami, G. S. Science 1995, 268, 397-400.
Sato, O.; Iyoda, T.; Fujishima, A.; Hashimoto, K. Science 1996, 272, 704-705.
Holmes, S. M.; Girolami, G. S. J. Am. Chem. Soc. 1999, 121, 5593-5594.
Kaye, S. S.; Long, J. R. J. Am. Chem. Soc. 2005, 127, 6506-6507. (b) Chapman, K. W.; Southon, P. D.; Weeks, C. L; Kepert, C. J. Chem. Commun. 2005, 3322-3324.
Smith, J. A.; Galan-Mascaros, J. R.; Cle'rac, R.; Sun, J. S.; Xiang, O. Y.; Dunbar, K. R. Polyhedron 2001, 20, 1727-xxx. (b) Berlinguette, C. P.; Dragulescu-Andrasi, A.; Sieber, A.; Glüdel, H. U.; Achim, C.; Dunbar, K. R. J. Am. Chem. Soc. 2005, 127, 6766-6779.
Heydlauf, H. Eur. J. Pharmacol. 1969, 6, 340-344. (b) Thompson, D. F.; Church, C. O. Pharmacotherapy 2001, 21, 1364-1367.
Nakamoto, K. Infrared and Raman Spectra of Inorganic and coordination Compounds Part B: Applications in Coordination, Organometallic and Bioinorganic Chemistry 5th Ed. pp. 60. John Wiley & Sons, Inc. 1997.
Edwards C. L. J. Nucl. Med. 1969, 10, 103 (b) Breeman, W. A. P.; Verbruggen, A. M. Eur. J. Nucl. Med. Mol. Imaging 2007, 34, 978-981.
International Application No. PCT/US11/25685 International Search Report/Written Opinion, Nov. 28, 2011, 11 pages.
Broschova et al, Czechoslovak Journal of Physics, vol. 52, No. 2, pp. 325-328, (2002).
Livramento, et al, High Relaxivity Confined to a Small Molecular Space: . . . , Angew. Chem. Int. Ed, 2005, vol. 44, pp. 1480-1484, Wiley-VCH Verlag GmbH & Co, Weinheim.
Werner, et al., High-Relaxivity MRI Contrast Agents: Where Coordination . . . , Angew. Chem. Int. Ed 2008, vol. 47, pp. 8568-8580, Wiley-VCH Verlag Gmbh & Co., Weinheim.
Bottrill, et al., Lanthanides in magnetic resonance imaging, Chem. Soc. Rev., 2006, vol. 35, pp. 557-571, The Royal Society of Chemistry, published on web.
International Application No. PCT/US11/25685 International Search Report/Written Opinion, Feb. 22, 2011, 11 pages.

\* cited by examiner

MATERIALS AND METHODS FOR MRI CONTRAST AGENTS AND DRUG DELIVERY

CROSS-REFERENCE TO RELATED APPLICATION/INCORPORATION BY REFERENCE

This U.S. patent application claims the benefit of and priority to provisional U.S. Patent Application Ser. No. 61/154,457 filed on Feb. 23, 2009, which is incorporated herein by reference in it entirety.

TECHNICAL FIELD

The invention relates generally to contrast agents used in medical imaging applications, and more particularly to MRI contrast agents and drug delivery platform created from Prussian blue materials.

BACKGROUND

Medical imaging modalities allow the visualization of the organs within a human body. For example, computed tomography (CT) also known as computed axial tomography (CAT): employs X-rays to produce 3D images. There are tens to hundreds of millions of scans done annually worldwide. Although non-invasive, CT is regarded as a moderate to high radiation diagnostic technique.

Another example of medical imaging technology is positron emission tomography (PET) and single photon emission computed tomography (SPECT). PET and SPECT use a short-lived radioactive isotope that undergoes a decay to emit a positron or gamma rays. There are tens to hundreds of millions of diagnostic medical procedures done every year. Both techniques expose the patient to low-level radiation and therefore impose risk to the patient.

A further medical imaging technology is magnetic resonance imaging (MRI). MRI uses a powerful magnetic field to align the nuclear magnetization of protons in water. It provides much greater contrast than does CT. Again, many millions of MRI exams are given annually.

Magnetic resonance imaging (hereinafter referred to as "MRI") has emerged as a prominent noninvasive diagnostic tool in clinical medicine and biomedical research. Among its many advantages, MRI can produce images with large contrast to visualize the structure and function of the body. It provides detailed images of the body in any plane. MRI generally provides much greater contrast between different soft tissues of the body as compared to other techniques, making it particularly useful in musculoskeletal imaging, cardiovascular and vascular imaging, neurological imaging, oncological imaging and other body parts or functions and diseases. Unlike CT or PET, MRI uses no ionizing radiation, but instead uses a magnetic field to align the nuclear magnetization of atoms (usually hydrogen atoms) in the body. The MRI imaging techniques therefore provide high quality images without exposing the patient to any kind of harmful radiation. The diagnostic power of MRI can be further enhanced with the use of a contrast agent. It is estimated that about 30% of all clinical MRI diagnostic examinations are performed with the intravenous injection of a contrast agent. This constitutes millions of doses of MRI contrast agent administered worldwide annually.

In magnetic resonance imaging (MRI) an image of an organ or tissue is obtained by placing a subject in a strong magnetic field and observing the interactions between the magnetic spins of the protons and radiofrequency electromagnetic radiation. The magnetic spins produce an oscillating magnetic field which induces a small current in the receiver coil, wherein this signal is called the free induction decay (FID). Two parameters, termed proton relaxation times, are of primary importance in the generation of the image. They are called $T_1$ (also called the spin-lattice or longitudinal relaxation time) and $T_2$ (the spin-spin or transverse relaxation time). The time constant for the observed decay of the FID is called the $T_2^*$ relaxation time, and is always shorter than $T_2$. The $T_1$, $T_2$ and $T_2^*$ relaxation times depend on the chemical and physical environment of protons in various organs or tissues.

In some situations or tissues, the MRI image produced may lack definition and clarity due to a similarity of the signal from different tissues or different compartments within a tissue. In some cases, the magnitude of these differences is small, limiting the diagnostic effectiveness of MRI imaging. Image contrast is created by differences in the strength of the NMR signal recovered from different locations within the tissue or sample. This depends upon the relative density of excited nuclei (such as water protons), on differences in the relaxation times $T_1$, $T_2$ and $T_2^*$ of those nuclei. The type of imaging pulse sequence may also affect contrast. The ability to choose different contrast mechanisms gives MRI tremendous flexibility. In some situations, the contrast generated may not adequately show the tissues, anatomy or pathology as desired, and a contrast agent may enhance such contrast. Thus, there exists a need for improving image quality is through the use of contrast agents.

Contrast agents are substances which exert an effect on the nuclear magnetic resonance (NMR) parameters of various chemical species around them. Ordinarily, these effects are strongest on the species closest to the agent, and decrease as the distance from the agent is increased. Thus, the areas closest to the agent will possess NMR parameters which are different from those further away. Proper choice of a contrast agent will, theoretically, result in uptake by only a certain portion of the organ or a certain type of tissue (e.g., diseased tissues), thus providing an enhancement of the contrast, which in turn generates a more accurate image. Contrast agents for MRI that are available may be injected intravenously to enhance the appearance of tumors, blood vessels and/or inflammation for example. Contrast agents may also be directly injected into a joint, for MR images of joints, referred to as arthrograms. Contrast agents may also be taken orally for some imaging techniques. Contrast agents generally work by altering the relaxation parameters, $T_1$, $T_2$ or $T_2^*$, such as by shortening these relaxation times.

Since MRI images can be generated from an analysis of the $T_1$, $T_2$ or $T_2^*$ parameters discussed above, it is desirable to have a contrast agent which affects either or both parameters. Much research has, therefore, centered around two general classes of magnetically active materials: paramagnetic materials (which act primarily to decrease $T_1$) and ferromagnetic materials (which act primarily to decrease $T_2$).

Paramagnetism occurs in materials that contain unpaired electrons which do not interact and are not coupled. Paramagnetic materials are characterized by a weak magnetic susceptibility, where susceptibility is the degree of response to an applied magnetic field. They become weakly magnetic in the presence of a magnetic field, and rapidly lose such activity (i.e., demagnetize) once the external field is removed. It has long been recognized that the addition of paramagnetic solutes to water causes a decrease in the $T_1$ parameter.

Because of such effects on $T_1$ a number of paramagnetic materials have been used as NMR contrast agents. However, a major problem with the use of contrast agents for imaging is that many of the paramagnetic and ferromagnetic materials exert toxic effects on biological systems making them inappropriate for in vivo use. Because of problems inherent with the use of many presently available contrast agents, there exists a need for new agents adaptable for clinical use. In order to be suitable for in vivo diagnostic use, such agents must combine low toxicity with an array of properties including superior contrasting ability, ease of administration, specific biodistribution (permitting a variety of organs to be targeted), and a size sufficiently small to permit free circulation through a subject's vascular system or by blood perfusion (a typical route for delivery of the agent to various organs). Additionally, the agents must be stable in vivo for a sufficient time to permit the clinical study to be accomplished, yet capable of being ultimately metabolized and/or excreted by the subject.

A $T_1$ agent primarily acts to brighten up the tissues where the agent is present due to its ability to enhance the longitudinal relaxation rate of protons from water ($1/T_1$). All the $T_1$ contrast agents currently used in clinical MRI imaging are gadolinium-based paramagnetic complexes with various polyaminopolycarboxylate ligands. 4-8 Gadolinium (Gd) is a rare-earth metal that can form a stable 3+ ion with 7 unpaired electrons ($4f^7$, $S=7/2$), the highest number of unpaired electrons (or magnetic spins) per metal center obtainable by any metallic element in the periodic table. FIG. 1 shows the structures of several typical Gd-based MRI contrast agents approved for clinical applications so far. The most noticeable feature in all these complexes is the water coordination to the metal center, which provides an important mechanism for enhancing the proton's longitudinal relaxation rate for this water and the surrounding water molecules.

Although gadolinium-enhanced tissues and fluids appear brighter on $T_1$-weighted images, which provides high sensitivity for detection of vascular tissues (e.g. tumors) and permits assessment of brain perfusion (e.g. in stroke), such compounds also have problems and risks. The relaxivity decreases with increasing magnetic field, and thus higher dosages are required to achieve the same contrast with higher magnetic fields. There have been concerns raised regarding the toxicity of gadolinium-based contrast agents and their impact, particularly on people with impaired kidney function. Both the free $Gd^{3+}$ ions and the polyaminopolycarboxylate ligand molecules used to sequester the metal ions exhibit in vivo toxicity.

Previously, it was assumed that the formation of a chelate between the metal ions and the ligand molecules with high thermodynamic stability and kinetic inertness can prevent the complexes from falling apart, thus reducing the toxicity. Unfortunately, the complex biochemical, pharmacokinetic and metabolic properties of such chelates often render the in vitro working model based on the thermodynamic and kinetic stability considerations inadequate for predicting their in vivo safe delivery. Use of these compounds has been linked to nephrogenic systemic fibrosis (NSF) and nephrogenic fibrosing dermopathy (NFD) for example. The renal toxicity of such agents has also prompted the US FDA to issue a public health advisory regarding the risk of using such agents. Additionally, such compounds are not possible to take orally, requiring intravenous administration, and do not act intracellularly but only extracellularly, thereby limiting their effectiveness.

The second type of contrast agents (i.e. $T_2$ agents) that have been recently approved for clinical use is from the family of iron oxide nanoparticles as shown in FIG. 2. These include superparamagnetic iron oxides (SPIO; 50-500 nm) and ultrasmall superparamagnetic iron oxides (USPIOs; 5-50 nm). In contrast to Gd-based MRI contrast agents, iron oxide nanoparticles can only increase the transverse relaxation rate of protons from water ($1/T_2$), thus producing darkened spots in the tissues where the material is present. From the standpoint of clinical diagnostic imaging, $T_2$ agents produce much less useful information. Thus, the primary application of the $T_2$ agents is for imaging-guided drug delivery and the monitoring of surgical procedures. Such materials have also been used for liver imaging, as normal liver tissue retains the agent, but abnormal areas (e.g. scars, tumors) do not. Other agents such as diamagnetic agents such as barium sulfate have also been studied for potential use in the gastrointestinal tract, but are less frequently used.

It should be noted that both the Gd-based $T_1$ agents and iron oxide-based $T_2$ agents are unstable in the acidic environment of the stomach, which has prevented them from being ever considered for oral delivery. Consequently, these materials can only be intravenously administered. In order to develop any new $T_1$ agent, the water molecules from the surroundings need to be able to exchange with the inner-sphere water molecules, and reside on the metal sites on and off, which can provide a mechanism for water's protons to significantly shorten their $T_1$ relaxation time, thus increasing the proton's magnetic resonance signal intensity (i.e. imaging contrast).

It would be desirable to provide MRI contrast agents which alleviates concerns with known agents and allows high contrast images to be achieved, with low toxicity. It would also be desirable to provide a MRI contrast agent that provides specific biodistribution, cellular imaging and permits free circulation through a patient's vascular system. Further, the qualities of ease of administration, such as by oral delivery methods, and providing stability in vivo for a sufficient time to permit the clinical study to be accomplished, while being ultimately metabolized and/or excreted by the subject, are needed. It would also be advantageous to provide a contrast agent that may allow both $T_1$ and $T_2$ imaging techniques to be performed.

There is also a need for drug delivery materials that allow drugs or other therapeutic agents to be delivered to tissues or portions of the body in an effective manner. There is also a need for agents that allow drugs or other therapeutic agents to be introduced into cells of the body.

SUMMARY

The invention is therefore directed to a new class of materials for use as MRI contrast agents or as a drug delivery platform, and relates to the use of bulk materials or nanoparticles of Prussian blue compounds. The Prussian blue compounds and methods of the invention provide effective MRI contrast agents which are able to be administered orally as well as intravenously for example, and cellular imaging. The Prussian blue nanoparticles may have the form of $Fe_4^{III}[Fe^{II}(CN)_6]_3 \cdot nH_2O$ (herein abbreviated throughout the disclosure as "PB"), and may be effective for specific biodistribution (permitting a variety of organs to be targeted for contrast enhancement and/or drug delivery), and have a size sufficiently small to permit free circulation through a subject's vascular system (a typical route for delivery of the agent to various organs). Additionally, the agents must be stable in vivo for a sufficient time to permit the clinical study to be accomplished, yet capable of being ultimately metabolized and/or excreted by the subject. The Prussian blue (PB) materials, either the bulk form or as nanoparticles with the size ranging from 1 to 500 nm or 10 to 300 nm for example, may be used as a $T_1$-weighted and/or T2-weighted MRI contrast agent. The PB nanoparticles according to the invention can be readily internalized by biological cells, allowing cellular imaging.

The approach of using PB materials as MRI contrast agents provides advantages over the paramagnetic materials and superparamagnetic iron oxide materials and represents a new class of agents useful in the design and synthesis of new MRI contrast agents. As background, Prussian blue has been used as a pigment in industry and for artists since 1704. On Oct. 2, 2003, the US Food and Drug Administration (FDA) determined that Prussian blue capsules, manufactured and marketed by HEYL Chemisch-pharmazeutische Fabrik GmbH & Co. KG as Radiogardase™, were found safe and approved its use for the treatment of internal contamination with radioactive cesium, radioactive thallium, or non-radioactive thallium in humans.

The presently disclosed PB materials and methods provide for use as contrast agents in cellular imaging techniques and in drug delivery applications. As the Prussian blue materials may be taken up by cells through endocytosis, cellular imaging is possible as opposed to blood perfusion, and drug delivery may be accomplished. Endocytosis is the process by which cells absorb material (molecules such as proteins) from outside the cell by engulfing it with their cell membrane. It is used by all cells of the body because most substances important to the cells are large polar molecules that cannot pass through the hydrophobic plasma membrane or cell membrane. As used throughout this disclosure, a "patient" or "subject" to be treated by the subject method can mean either a human or non-human subject.

In summary, the invention provides materials and methods for use as contrast agents for imaging of a human or animal organs or tissues or delivering drugs to human or animal organs or tissues, and comprises Prussian blue materials formed into nanoparticles. The PB materials may also be used as a platform for simultaneous imaging and drug delivery. Further, the invention may be adapted for oral delivery of the MRI contrast agent as the PB materials are shown to be non-toxic and stable in strong acidic environments.

The presently disclosed invention also relates to a method of generating an image of a human or a non-human animal subject involving administering a contrast agent to said subject and generating an image of at least a part of said subject to which said contrast agent has been distributed, wherein the contrast agent is a composition of matter of Prussian blue materials. Further, also disclosed is a process for the preparation of a contrast agent of one or more Prussian blue nanoparticles, with the process comprising the steps of combining a concentration of a ferric salt or a ferrous salt with a concentration of a soluble ferriccyanide ($[Fe^{III}(CN)_6]_{3-}$) or a soluble ferrocyanide ($[Fe^{II}(CN)_6]_{4-}$) to create a precursor solution; and adding a surface capping agent to the precursor solutions. The surface capping agent may be a carboxylic compound according to an example. Other materials and methods are provided according to the invention.

BRIEF DESCRIPTION OF DRAWINGS

FIG. 3c shows T2 contrast at repetition time $t_r$=5000 ms and echo time $t_e$=50 ms.

DESCRIPTION OF EXAMPLES OF THE INVENTION

Figure 1:
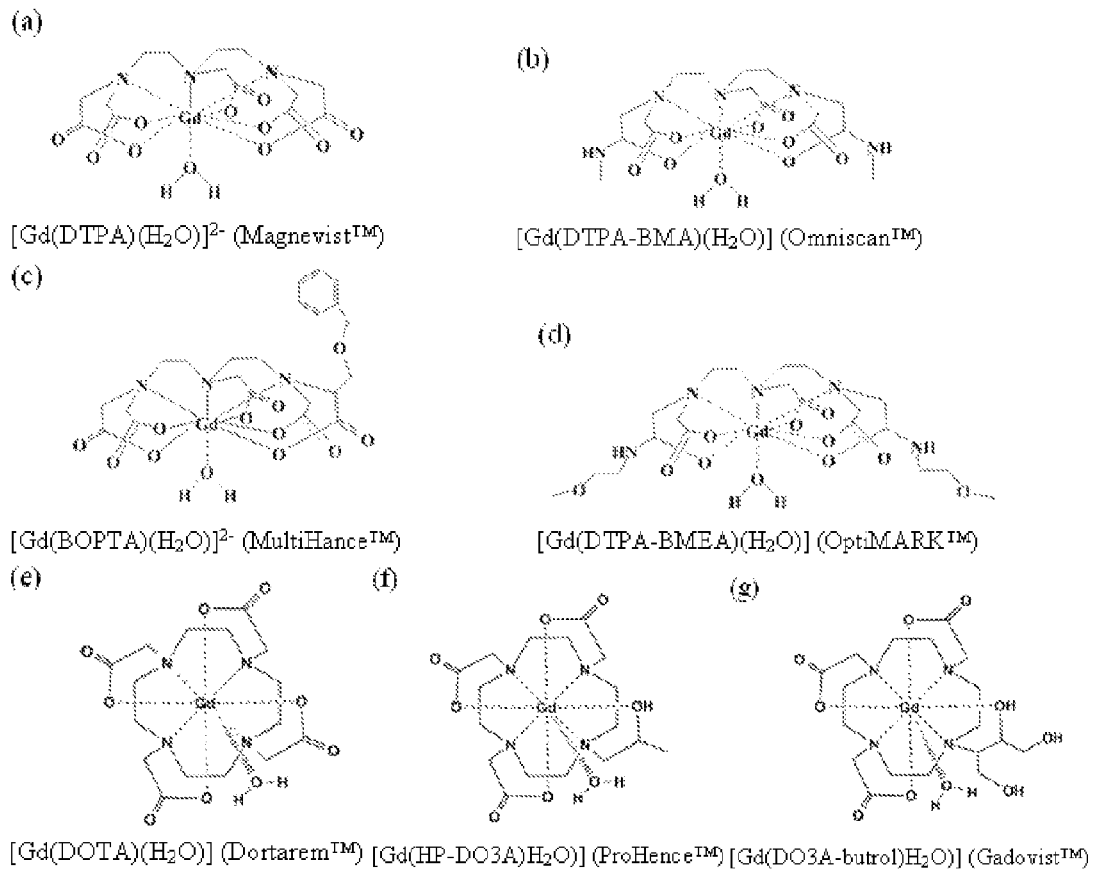
FIG. 1a-1g are several views of the chemical structures of several known Gd-based MRI contrast agents.

The present invention relates to compositions of Prussian blue (hereinafter referred to as "PB") materials as contrast agents for medical imaging or as vehicles for drug delivery, and methods relating to the use thereof.

PB belongs to the class of iron hexacyanoferrate (II). PB is known by the chemical formula:

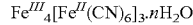
$$Fe^{III}_4[Fe^{II}(CN)_6]_3 \cdot nH_2O$$

In the chemical formula for PB, the value n represents an integer in the range from 1 to about 24. The PB materials according to the invention may have a composition of the chemical compound:

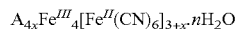
$$A_{4x}Fe^{III}_4[Fe^{II}(CN)_6]_{3+x} \cdot nH_2O$$

The value A may be selected from the group consisting of Lithium (Li+), Sodium (Na+), Potassium (K+), Rubidium (Rb+), Caesium (Cs+), Ammonium (NH$_4$+) and Thallium (Tl+). The value x may range any where between $0 \leq x \leq 1$, and the value n represents an integer in the range 1 to about 24, and more particularly between 14-16. Any particular composition in this class may be used as the MRI contrast agents or drug delivery systems according to the invention. The PB compound may be a soluble compound or an insoluble compound, wherein the insoluble compound is characterized by coordinating water molecules therein.

Prussian blue is a mixed-valence iron hexacyanoferrate with the approximate formula as set forth above. The synthesis of PB nanoparticles may be performed using different variations of the multi-component reverse micelle technique or the direct precipitation process in a polymeric or a biological matrix for example, but any suitable technique is contemplated. Such techniques could be used according to the invention to prepare PB nanoparticles of a predetermined size, but the invention also provides a simple aqueous solution route for preparing PB nanoparticles. This process does not require the use of any organic or polymeric additives as are needed for the formation or water-in-oil microemulsion or as a template, but otherwise may be nonbiocompatible. The process will be described further hereafter, but provides a simple and cost-effective approach to forming the materials for use according to the invention.

The PB materials are magnetic, non-toxic and can enter cells by endocytosis. For purposes of experiment only, two different types of PB nanoparticles with the diameters of 25 nm and 50 nm respectively were prepared and selected for relaxivity measurements, cellular imaging and all bioassaying. The use of PB nanoparticles as MRI contrast agents does not raise concern about its chemical toxicity because the CN$^-$ ligands in PB are completely locked in their lattice positions and cannot be released from the compound, due to the strong ligand-field effect, when simultaneously bound to both ferric and ferrous ions in an extended 3D coordination network structure. The PB compound has a low solubility product constant ($K_{sp}=10^{-41}$) as noted, and has been found safe for oral delivery for the treatment of internal contamination with radioactive cesium, radioactive thallium, or non-radioactive thallium in humans. The PB materials according to the invention may thus be administered parenterally via intravenous or intramuscular injection, or by oral delivery because the PB materials are well tolerated and non-toxic at acceptable dosage levels, are able to withstand and are stable in highly acidic environments such as the gastrointestinal tract. The PB materials are generally excreted by the body in about two days.

Chemical Terms

The term "carboxylic acid" are organic acids characterized by the presence of a carboxyl group and are recognized by a person of skill in the art and include such moieties as can be represented by the general formula: —C(=O)OH, usually written —COOH or —CO2H. In the simplest chemical form, carboxylic acids are also known by as alkanoic acids, wherein the formula is R—COOH, where R is a hydrogen or an alkyl group. Carboxylic acid compounds may also have two or more carboxylic acid groups per molecule.

For purposes of this invention, the chemical elements are identified in accordance with the Periodic Table of the Elements.

The PB materials may be used to create a $T_1$ weighted contrast agent, or positive contrast agent that causes a reduction in the $T_1$ relaxation time (increased signal intensity on $T_1$ weighted images). A $T_1$ contrast agent may be developed by exchanging the water molecules from the surrounding environment with the inner-sphere water molecules that reside on the metal sites on and off. This provides a mechanism for water's protons to significantly shorten their $T_1$ relaxation time, thus increasing the proton's magnetic resonance signal intensity (i.e. imaging contrast).

Figure 2:
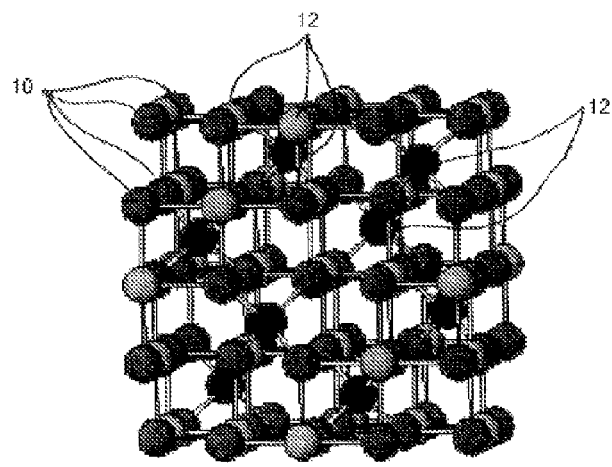
FIG. 2 is the crystal structure of known superparamagnetic iron oxide $Fe_3O_4$ nanoparticles.

The PB materials may also be used to create a $T_2$ weighted contrast agent. In known $T_2$ contrast agents, such as superparamagnetic iron oxide (SPIO) $Fe_3O_4$ nanoparticles, the compound forms a dense magnetite structure as shown in FIG. 2 in which the Fe metal centers are inaccessible for $H_2O$ coordination, but the material is magnetic, thus giving the outer-sphere relaxivity enhancement of $T_2$. In FIG. 2, the oxygen atoms are shown at 10 while the iron atoms are shown at 12, with iron atoms 12 shown to be inaccessible in the lattice structure. In general principle, a $T_2$ agent cannot be converted into a $T_1$ agent, or to combine the attributes of both $T_1$ and $T_2$ agents into a single compound, unless the new compound can simultaneously provide a strong local magnetic field (like iron oxide nanoparticles) as well as water coordination sites on the individual metal centers (like a Gd-based complex). Such materials again have deficiencies, as being a $T_2$ MRI contrast agent primarily acts to darken the tissue areas, which can adversely affect the diagnostic or other features of the image. Further, the SPIO nanoparticles can readily accumulate in the liver and spleen, and such materials are also administered parenterally, such as by intravenous or intramuscular injection. Although the materials can be distributed cellularly, as a $T_2$ agent, such materials still have significant drawbacks. In the present invention, the ability to of the PB compounds to be both $T_1$ and $T_2$ agents provides flexibility in conjunction with RF pulse sequences to achieve desired contrast enhancement. Also, due to the very small particles of less than 500 nanometers, or in a further example, less than 300 nanometers, the materials may remain intravascular for a prolonged period of time and thus may serve as blood pool agents. The materials may also be suitable for magnetic resonance angiography (MRA), cardiovascular imaging or contrast enhanced MRI's for example.

General Procedure for Preparation of Prussian Blue Materials

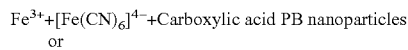

or

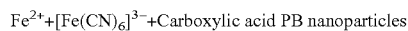

Suitable procedures for forming Prussian Blue nanoparticles of a desired size may be implemented in a known manner, and may be used to form the nanoparticles according to the invention. It is to be understood throughout this description of the invention, that the use of Prussian Blue materials as MRI contrast agents is but one embodiment of the invention and that the PB materials in either bulk form or nanoparticle form may be used for other medical applications such as cellular imaging or drug delivery applications. The Prussian Blue materials synthesized according to the invention may be a $T_1$-weighted magnetic resonance imaging contrast agent or as a $T_2$-weighted magnetic resonance imaging contrast agent, or an agent which can be used simultaneously for imaging and drug delivery.

For the preparation of the PB materials and PB nanoparticles a synthesis may be carried out in an aqueous solution. An aqueous solution is defined as a solution in which the solvent is water. The word aqueous is defined as pertaining to, related to, similar to, or dissolved in water. A proper concentration [$10^{-3}$ to $10^3$ M for example] of a ferric salt or a ferrous salt is mixed with a proper concentration [$10^{-3}$ to $10^3$ M for example] of soluble ferriccyanide ([$Fe^{III}(CN)_6]_{3-}$) or a soluble ferrocyanide ([$Fe^{II}(CN)_6]_{4-}$) to form one or more precurs The ferric salt or the ferrous salt may be selected from the group consisting of a chloride, a sulfate of iron (II), or a sulfate of iron (III) (or any other soluble salt of iron (II) or iron (III)). The process of forming the PB nanoparticles may be by a simple aqueous solution route which circumvents the use of any organic or polymeric additive that would be used for the formation of water-in-oil microemulsion or as the template, but otherwise may be nonbiocompatible. The method utilizes the complexation of the ferric ions by a carboxylic acid as the precursor to reduce the rate of nucleation when this precursor reacts with ferrocyanide. As the PB nanoparticles begin to form in situ, the same carboxylic acid can act as a surface-capping agent to control the size and prevent agglomeration. This approach is reminiscent of using ammonium iron(III) citrate to modulate the photochemical reaction rate of PB formation in cyanotype by UV irradiation. Other suitable techniques to form the PB nanoparticles may be used.

As an example, citrate-coated PB nanoparticles were prepared by slowly adding 20 mL of 1.0 mM $FeCl_3$] solution containing 10 mmol of citric acid into an equimolar $K_4$[Fe (CN)$_6$] solution containing 10 mmol of citric acid under rigorous stirring at room temperature. The product was isolated by centrifugation and washing with a water-acetone mixture (50:50 v/v) for three times. X-ray powder diffraction studies showed that all the peaks can be indexed into the cubic face-centered PB phase (space group Fm3m). No other peaks attributable to the formation of small-molecule metal carboxylate clusters were found. Transmission electronic microscopy (TEM) examinations revealed that the nanoparticles are well-separated and narrowly distributed with an average diameter of ca. 13 nm in an example. Dynamic light scattering (DLS) measurements showed the hydrodynamic diameter of the PB nanoparticles to be 25 nm as an example. In the PB nanoparticles formed according to this example, the FT-IR spectra of the PB nanoparticles in the KBr matrix exhibit a strong characteristic CN stretching vibration at 2078 cm$^{-1}$ for $Fe^{2+}$—CN—$Fe^{3+}$ in the coordination polymer lattice. In addition, the asymmetric and symmetric carboxyl stretching bands were observed at 1712 and 1364 cm$^{-1}$ with Δ [$v_a$(COO)–$v_s$(COO)]=348, which is indicative of asymmetric metal-carboxylate coordination. The resonance Raman spectra of the PB nanoparticles dispersed in aqueous solution contained essentially the same spectroscopic feature. The results from thermal gravimetric analysis (TGA) and elemental analysis of C, H, N and Fe showed the average load of citrate to be 7.4 wt %.

A surface capping agent may be added to either one of the above-mentioned precursor solutions or both before mixing the solutions. The surface capping agent may be used to control the growth of the PB materials in the nanometer region. The surface capping agent may be a biocompatible carboxylic compound. The carboxylic compounds may include, but are not limited to carboxylic acids such as acetic acid, oxalic acid, citric acid, tartaric acid, adipic acid, gluconic acid, and other mono-, di-, tri- or polycarboxylic acids. The use of a carboxylic acid capping agent allows effective control of the size of the nanoparticles and stabilizes the PB nanoparticles. Direct mixing of equimolar $FeCl_3$ and $K_4[Fe(CN)_6]$ solutions under the same conditions in the absence of any capping agent, such as carboxylic acid, resulted in the formation of PB nanoparticles with the widely distributed size larger than 100 nm for example, although other techniques of controlling the size of the nanoparticles may be used. Furthermore, it was found that without the capping agent, such particles can aggregate to form precipitate containing particles larger than 300 nm in about two hours. When a carboxylic acid is used as a capping agent, three different synthetic parameters can be tuned independently or simultaneously, i.e. the type of carboxylic acid used, the concentrations of the precursors $Fe^{3+}/[Fe(CN)_6]^{2-}$, and the ratio of the precursor ions to the capping agent can all affect the particle size, size distribution and surface stability. Using this simple strategy, stable PB nanoparticles were obtained capped by tartrate, salicylate or mycophenolate (an immunosuppressant and anticancer agent) respectively with the size ranging from 10 to over 100 nm for example. The synthesis route allows an in situ method of conjugating a drug molecule containing carboxyl functionality to a PB nanoparticle surface.

The stability of citrate-coated PB nanoparticles that were exposed in air in the solid-state or as an aqueous dispersion was monitored over six months by visual inspection, FTIR, elemental analysis and TGA. No change in the particle size, size distribution, dispersibility and surface coating was detected during this time period. Although a strong HCl solution (>1 M) can strip the surface carboxylate coating and cause the nanoparticles to aggregate, the bulk PB formed from this treatment remains stable in 12 M HCl and aqua regia.

Fluorescence-labeling of the PB nanoparticles may be conducted by using an organic dye molecule that contains at least one carboxylic acid functional group. The method also provides a process for dye-labeling Prussian blue materials in order to image the subject using fluorescence microscopy. The process for dye-labeling the PB materials is similar to the process described above for creating the PB nanoparticles. For the preparation of the dye-labeled PB materials, the dye-labeled PB materials may be synthesized by combining a concentration of a ferric salt or a ferrous salt with a concentration of a soluble ferriccyanide ($[Fe^{III}(CN)_6]_{3-}$) or a soluble ferrocyanide ($[Fe^{II}(CN)_6]_{4-}$) to create one or more precursor solutions. A surface capping agent may then be added to the precursor solutions. In order to dye-label the PB materials, a dye molecule may be added to the precursor solution in the place of the surface capping agent or in combination with the surface capping agent. The dye molecule may have at least one carboxylic acid functional group in the compound. The dye molecule containing at least one carboxylic acid functional group may be selected from the group consisting of fluorescein (or Texas Red cadaverine (Texas Red® $C_5$) or its chemical derivatives for example. The dye-labeled Prussian blue nanoparticles may be used as a cellular fluorescence imaging agent in fluorescence microscopy. The dye-labeled Prussian blue materials may be used as a dual modality MRI-Fluorescence imaging agent.

The synthetic methods according to this invention provide for convenient preparation of biocompatible PB nanoparticles with the size ranging from 5 to 300 nm for example, but other suitable sizes or the bulk material could be used. The synthetic methods according to the present invention may not rely on the use of the reverse micelle technique (i.e. the formation water-in-oil microemulsions) as in other techniques, or the use of a polymer as a coating agent (e.g. polyvinylpyrrolidine). These approaches require the use of undesirable nonbiocompatible surfactants and organic additives necessary for the formation of water-in-oil emulsions. The synthesis method of the present invention circumvents the use of any of such additives. More specifically, the invention uses simple, nontoxic and biocompatible carboxylic acids as a surface-capping agent to form the nanoparticles, which is sufficient to control the growth of PB materials in the nanometer region. The carboxylic acids that can be used as the surface-capping agent include, but are not limited to, acetic acid, oxalic acid, citric acid, tartaric acid, adipic acid, gluconic acid, and other mono-, di-, tri- or polycarboxylic acids. As described, the synthesis can be carried out in an aqueous solution by mixing the solution of a ferric or ferrous salt such as chloride or sulfate of iron (II) or iron (III) (or any other soluble salt of iron (II) or iron (III)) with a proper concentration, with a soluble ferriccyanide ($[Fe^{III}(CN)_6]_{3-}$) or a soluble ferrocyanide ($[Fe^{II}(CN)_6]_{4-}$) with a proper concentration. The carboxylic acid capping agent may be added to either one of the above-mentioned precursor solutions or both before mixing the solutions. Fluorescence-labeling of the PB nanoparticles using an organic dye molecule that contains at least one carboxylic acid functional group (such as fluorescein) can be carried out using our synthetic method in a similar fashion as the above. The dye molecule can be directly used in the place of a carboxylic acid capping agent or in combination with a carboxylic agent capping agent. The dye-labeled PB nanoparticles can therefore be used as a cellular fluorescence imaging agent alone or as a bi-modal MRI-Fluorescence imaging agent.

Figure 3:
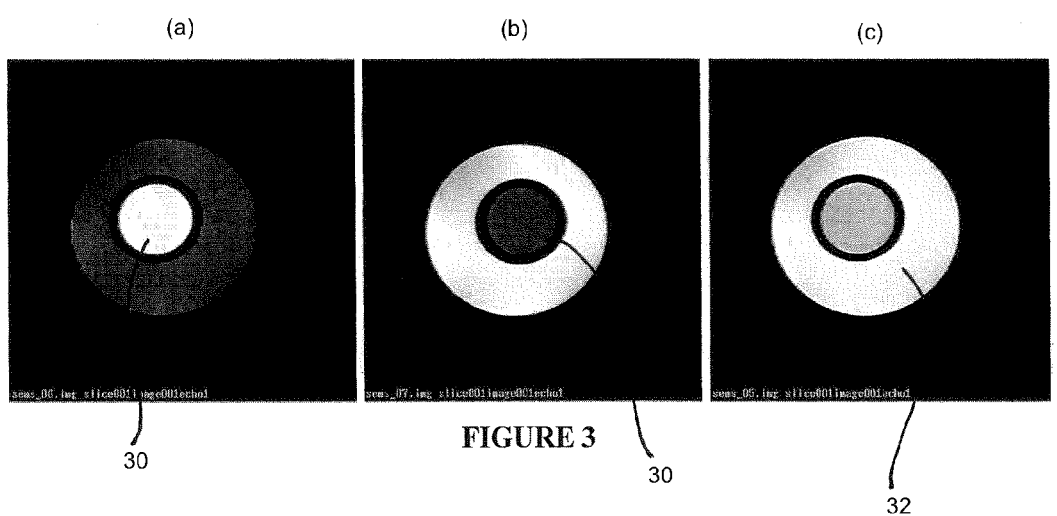
FIGS. 3a, 3b, and 3c are pictures of MRI slices for contrast agent in internal (3a), (3b) and external (3c) tubes respectively. The FIGS. 3a and 3b show $T_1$ contrast at repetition time $t_r$=500 ms and echo time $t_e$=20 ms.

This invention describes a new class of non-gadolinium and non-iron oxide based nanoparticles, with the size in the range of 1 to 500 nm, or more particularly to 5 to 300 nm, that can be used as $T_1$-weighted or $T_2$-weighted MRI contrast agents for cellular imaging in clinical diagnosis and biomedical research applications. The PB MRI contrast agents are highly effective, non-toxic, and can be internalized by cells through endocytosis. Their stability in strong acidic media makes them suitable for oral delivery to the human or non-human body. The PB contrast agent allows use for both $T_1$-weighted or $T_2$-weighted MRI contrast agents due to the compound simultaneously providing a strong local magnetic field (like iron oxide nanoparticles) as well as water coordination sites on the individual metal centers (like a Gd-based complex). The synthesis of the PB compounds and the ability to control the size and functionalize the surface for tailor-making various PB nanoparticles in the range of 5 to 300 nm for example, allows use for MRI contrast agents and/or drug delivery or both. The PB materials are magnetic, non-toxic and can enter cells by endocytosis for intracellular imaging. FIG. 3 shows the imaging results of a phantom system of distilled water in tubes with and without the agent added. FIG. 3a shows a MRI slice showing the use of a contrast agent in accordance with the invention in an internal tube 30 as a $T_1$-weighted contrast at repetition time $t_r$=500 ms and echo time $t_e$=20 ms. The $T_1$-weighted MRI contrast enhancement by PB nanoparticles is seen from a slice of an internal NMR tube acquired using Varian's VNMRJ spin-echo multi-slice pulse sequence, showing significant brightening as compared to the tube 30 in FIG. 3*b* without contrast agent. FIG. 3*c* shows the PB contrast agent in the external tube 32 with $T_2$ contrast at repetition time $t_r$=5000 ms and echo time $t_e$=50 ms. The $T_2$-weighted MRI contrast enhancement by PB nanoparticles in FIG. 3*c* is seen from a slice of an internal NMR tube acquired using Varian's VNMRJ spin-echo multi-slice pulse sequence. The preliminary results of the measured longitudinal relaxivity of PB nanoparticles, $R_1$=2.6 per mM's is very comparable to the typical Gd-based agent of $R_1$=4.0 per mM's. Furthermore, the ability to be distributed intracellularly and by blood perfusion, and the stability in acidic media provides the characteristics for allowing a great amount of flexibility in use of the PB nanoparticles as contrast agents.

The PB-based MRI contrast agents of the invention provide $Fe^{3+}$ ions ($3d^5$, S=5/2) in the PB structure which resemble the $Gd^{3+}$ centers in the small molecular complex drugs in terms of water coordination and accessible cavities residing inside the structure. This feature allows for the longitudinal relaxation of protons to be operative. On the other hand, each PB nanoparticle acts as a small magnet, similar to the magnetic iron oxide nanoparticles for providing a local magnetic field, which enhances the $T_1$ relaxation as well as activates the transverse relaxation of water ($T_2$).

The cellular uptake of the PB nanoparticles was shown in association with the human cell line HeLa. The internalization of the PB nanoparticles may be visualized by dye-labeling of the PB nanoparticles and viewing using confocal microscopy. For example, Texas Red cadaverine (Texas Red® $C_5$) was conjugated to the citrate-coated PB nanoparticle surface by an EDC coupling reaction to form dye-conjugated PB nanoparticles (TRPBNPs for example). The dye-conjugated PB nanoparticles, TRPBNPs were dialyzed against a 3,000 MWCO membrane for three days to remove unreacted dye and analyzed by fluorescence spectrophotometry before incubating with the cells for various times. It was found the TRPBNPs were readily internalized into HeLa cells after 2 hours incubation. Confocal microscopy showed the presence of red fluorescent structures scattered in the cytoplasmic compartments of cells treated with TRPBNPs. Analysis of the lysate of the 24 h incubation by ICPMS indicated an amount of iron was in the cells, and the cellular internalization of the nanoparticles in HeLa took place without the assistance of a delivery agent, and by endocytosis.

Although the non-toxic nature of bulk PB is well known, the testing of biological actions of the PB nanoparticles was performed to determine whether they were also non-toxic at the cellular level. The cell viability of PB nanoparticles was performed using a trypan blue exclusion method. HEK-293 cells were incubated for 24 hours with varying concentrations of PB nanoparticles. At the approximate saturation concentration of PB nanoparticles of ~0.25 mg/mL, the cell viability was found to be ca. 96.98±85%, and thus the citrate-coated PB nanoparticles exhibit no significant cytotoxicity in cells.

The PB nanoparticles according to the invention were also analyzed via magnetization measurements at room temperature. Such measurements revealed a large susceptibility value without any hysteresis loop, suggesting a superparamagnetic behavior. In light of the wide applications of superparamagnetic iron oxides (SPIOs) in drug delivery, MR imaging and hyperthermia cancer treatment, the PB nanoparticles may be useful for related applications that SPIOs are used for, such as those mentioned or others.

The invention is also useful as a drug delivery platform. As used herein, a "drug" is defined as any therapeutically, prophylactically and/or pharmacologically or physiologically beneficial active substance, or mixture thereof, which is delivered to a living organism to produce a desired, usually beneficial, effect. More specifically, any drug which is capable of producing a pharmacological response, localized or systemic, irrespective of whether therapeutic, diagnostic, or prophylactic in nature, in plants or animals is within the contemplation of the invention. The drug may be pharmacologically active or may require further biotransformation. The term "drug" encompasses both "parent drug" and "prodrug". As used herein, a "parent drug" is defined the same as a "drug," except that it does not undergo biotransformation to render it more pharmacologically active. As used herein, a "prodrug" is defined as a pharmacologically less active derivative of a parent drug molecule that requires biotransformation, either spontaneous or enzymatic, within the organism to release the more active parent drug. Prodrugs are variations or derivatives of the parent drugs which have groups cleavable under metabolic conditions. Prodrugs become the parent drugs which are pharmaceutically active in vivo, when they undergo solvolysis under physiological conditions or undergo enzymatic degradation. Prodrugs may be called single, double, triple, etc., depending on the number of biotransformation steps required to release the active parent drug within the organism, and indicating the number of functionalities present in a precursor-type form. Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. See, Bundgard, Design of Prodrugs, pp. 7-9, 21-24, Elsevier, Amsterdam 1985; Silverman, The Organic Chemistry of Drug Design and Drug Action, pp. 352-401, Academic Press, San Diego, Calif., 1992; and Burger's Medicinal Chemistry and Drug Chemistry, Fifth Ed., Vol. 1, pp. 172-178, 949-982 (1995). As used herein, "pharmacologically equivalent amount" is defined as an amount of the parent drug or prodrug that has an equivalent therapeutic effect as a selected combined amount of the parent drug and prodrug. The drug should be used in amounts sufficient to prevent, cure, diagnose or treat a disease or other condition, as the case may be.

In accordance with such an example, the drug may be combined with the PB nanoparticles by incorporation of the drug into or onto the nanoparticles to improve the bioavailability of the drug. Bioavailability refers to the presence of drug molecules where they are needed in the body and where they will do the most good. Drug delivery focuses on maximizing bioavailability both at specific places in the body and over a period of time. This can be achieved by biodistribution of the PB nanoparticles and molecular targeting by the PB nanoparticles. Drug delivery systems may utilize the PB nanoparticles, which can be designed to be taken up by cells through endocytosis. Endocytosis is the process by which cells absorb material (molecules such as proteins) from outside the cell by engulfing it with their cell membrane. Where larger particles would have been cleared from the body, cells take up these PB nanoparticles because of their size. The PB nanoparticles may be designed to have the ability to get drugs through cell membranes and into cell in an efficient manner. As many diseases depend upon processes within the cell and can only be impeded by drugs that make their way into the cell. The PB nanoparticles may also be provided to generate a triggered response where drugs are placed in the body and only activate on encountering a particular signal. Also, the drug delivery system may regulate drug release, and clearance of the drug from the body can be reduced or controlled by altering the pharmacokinetics of the drug. Poor biodistribution is a problem that can affect normal tissues through widespread distribution, but the use of PB nanoparticles in a drug delivery system can lower the volume of distribution and reduce the effect on non-target tissue. Another property of the nanoparticles is that they provide a high surface area to volume ratio, which allows many functional groups to be attached to the PB nanoparticles. Such functional groups may then allow biotargeting, such as of tumor cells for treatment of cancer. The small size of the PB nanoparticles (10 to 100 nanometers), allows them to preferentially accumulate at tumor sites because tumors lack an effective lymphatic drainage system. Further, the PB nanoparticles could also be designed to be multifunctional, providing an image enhancing agent for MRI imaging of diseased tissues and then as a drug delivery platform to proceed to treat a disease. The PB nanoparticles may be designed to be used in drug delivery by enabling efficient encapsulation of the drugs, successful delivery of the drugs to a targeted region of the body, and to release the drug in a controlled manner.

For example, a number of metallic radionuclides have found applications in diagnostic or therapeutic radiopharmaceuticals. Delivery of such elements usually depends on complexation of the metal ion with a small-molecule ligand. We incorporated various amounts of $Ga^{3+}$ ions into the PB lattice to form nanoparticle solid solutions as a potential carrier to deliver radionuclide Ga-67 (γ-emitter with $t_{1/2}$=78.3 h) or Ga-68 (positron-emitter with $t_{1/2}$=68 m). Both of them have been employed in diagnostic nuclear medicine for γ-radiation or positron-emission imaging. Due to the identical charge and similar ionic radius, we found that the $Ga^{3+}$ ion can replace $Fe^{3+}$ in the PB structure to form stable solid solutions $A_{4x}(Ga_yFe_{1-y}^{III})_4[Fe^{II}(CN)_6]_{3+x} \cdot nH_2O$ $0 \leq y \leq 1$, in the entire concentration range. The particle size, size distribution and stability of the Ga(III)-Fe(III) solid-solution nanoparticles are virtually identical to the pure iron counterparts. The PB nanoparticles may thus be useful as an in vivo delivery agent of both Ga-67 and Ga-68, or other materials or agents, for drug delivery, molecular or cellular probes for spectroscopy and microscopy and nanomedicine application.

The PB nanoparticles and synthetic route for preparing biocompatible carboxylate-capped PB nanoparticles according to the invention are thus useful for a variety of applications. The PB nanoparticles provide stability, no significant cytotoxicity, and have the ability to penetrate cells. Further, the invention also relates to a large number of PB analogue compounds and solid solutions with the formula $A_{m-x}M'_m[M(CN)_6]_n$ where A is an alkali metal, M is a transition metal and M' is a main-group, transition or lanthanide metal. More particularly as an example, the one or more nanoparticles are formed as PB analogue compounds or solid solutions with the formula $A_{m-x}M'_m[M(CN)_6]_n$ where A is an alkali metal, M=Fe, Co or Mn and CN is a transition metal and M'=Fe or Co. The PB nanoparticles or PB analogue compounds and solid solutions provide diverse optical, photochemical, electrochemical and magnetic properties, for use as a platform for delivery vehicles for drugs, molecular or cellular probes for spectroscopy and microscopy, and contrast agents for various imaging modalities and other applications.

The materials and methods as described above are not to be construed as limiting the invention to any certain application or example. The contrast agent and imaging method, or drug delivery materials or methods disclosed herein may also be used for other medical imaging techniques, drug delivery applications, or other clinical diagnostic applications and biomedical research applications.

We claim:

1. An agent for imaging of a biological system or delivering drugs to a biological system comprising:
   a plurality of biocompatible nanoparticles formed of Prussian blue materials and without gadolinium and iron oxide, wherein a biocompatible surface capping agent controls the size of the plurality of nanoparticles.

2. The agent of claim 1, wherein the Prussian blue materials are an iron hexacyanoferrate (II) compound.

3. The agent of claim 1, wherein the Prussian blue materials are $A_{4x}Fe^{III}_4[Fe^{II}(CN)_6]_{3+x} \cdot nH_2O$ wherein A is selected from the group consisting of Li+, Na+, K+, Rb+, Cs+, NH4+ and Tl+; $0 \leq x \geq 1$; and the value n represents an integer in the range 1 to about 24.

4. The agent of claim 1, wherein the plurality of nanoparticles are within the size ranging from 5 nm to 300 nm.

5. The agent of claim 1, further comprising a biocompatible surface capping agent sufficient to control the growth of the Prussian blue materials in a nanometer region.

6. The agent of claim 5, wherein the surface capping agent may be selected from the group consisting of acetic acid, oxalic acid, citric acid, tartaric acid, adipic acid, gluconic acid, and mono-, di-, tri- or polycarboxylic acids or combinations thereof.

7. The agent of claim 1, further comprising providing the agent in a carrier to be introduced into the body, wherein the plurality of nanoparticles act as a $T_1$-weighted magnetic resonance imaging contrast agent.

8. The agent of claim 1, further comprising providing the agent in a carrier to be introduced into the body, wherein the plurality of nanoparticles act as a $T_2$-weighted magnetic resonance imaging contrast agent.

9. The agent of claim 1, wherein the Prussian blue materials may be administered orally to a subject.

10. The agent of claim 1, wherein the Prussian blue materials are compounds or solid solutions with the formula $A_{m-x}M'_m[M(CN)_6]_n$ where A is an alkali metal, M is a transition metal and M' is a main-group, transition or lanthanide metal.

11. The agent of claim 1, wherein the surface capping agent is a carboxylic acid.

12. The agent of claim 1, wherein the surface capping agent is selected from the group consisting of mono-, di-, tri- and polycarboxylic acids and combinations thereof.

13. The agent of claim 12, wherein the mono-carboxylic acid is acetic acid.

14. The agent of claim 12, wherein the di- or polycarboxylic acids are selected from the group consisting of oxalic acid, tartaric acid, adipic acid, gluconic acid and combinations thereof.

15. The agent of claim 12, wherein the tri-carboxylic acid is citric acid.

16. The agent of claim 1, wherein the agent is formulated to be administered orally to a subject.

17. The agent of claim 1, wherein the agent is formulated to be administered intravenously to a subject.

18. The agent of claim 1, wherein the Prussian blue nanoparticles are dye-labeled.

19. The agent of claim 1, wherein the plurality of nanoparticles are formed as Prussian blue compounds or solid solutions with the formula $A_{m-x}M'_m[M(CN)_6]_n$ where A is an alkali metal, M=Fe, Co or Mn and CN is a transition metal and M'=Fe or Co.

20. The agent of claim 19, wherein CN ligands are locked in their lattice positions and cannot be released from the compound to provide biocompatibility.

21. The agent of claim 1, wherein the plurality of nanoparticles of Prussian blue material have a low solubility product constant.

22. The agent of claim 1, wherein the plurality of particles are administerable to a body parenterally via intravenous or intramuscular injection, or by oral delivery.

23. The agent of claim 1, wherein the plurality of nanoparticles enter cells by endocytosis.

24. The agent of claim 1, wherein the plurality of particles are insoluble and characterized by coordinating water molecules therein.

25. The agent of claim 1, wherein the plurality of particles are stable in acidic media.

26. The agent of claim 1, wherein the Prussian blue nanoparticles include $Fe^{3+}$ ions ($3d^5$, $S=5/2$) in the structure to provide water coordination sites and accessible cavities residing inside the structure, thereby allowing for the longitudinal relaxation of protons as well as each nanoparticle providing a local magnetic field, which enhances the $T_1$ relaxation as well as activates the transverse relaxation of water ($T_2$).

27. The agent of claim 1, wherein the plurality of nanoparticles provide a high surface area to volume ratio, such that functional groups may be attached to the nanoparticles.

28. The agent of claim 27, wherein the functional groups allow biotargeting of predetermined cells.

29. An agent for imaging of a biological system or delivering drugs to a biological system comprising:
a plurality of biocompatible nanoparticles formed of Prussian blue materials and without gadolinium and iron oxide and wherein a biocompatible surface capping agent controls the size of the plurality of nanoparticles, wherein the particles include Fe3+ ions ($3d^5$, $S=5/2$) in the structure to provide water coordination sites and accessible cavities residing inside the structure, thereby allowing for the longitudinal relaxation of protons as well as each nanoparticle providing a local magnetic field.

30. An agent for imaging of a biological system or delivering drugs to a biological system comprising:
a plurality of biocompatible nanoparticles formed of Prussian blue materials and without gadolinium and iron oxide, wherein the plurality of nanoparticles have the formula $A_{m-x}M'_m[M(CN)_6]_n$ where A is an alkali metal, M=Fe, Co or Mn and CN is a transition metal and M'=Fe or Co, and wherein CN ligands are locked in their lattice positions and cannot be released from the compound to provide biocompatibility, and wherein a biocompatible surface capping agent controls the size of the plurality of nanoparticles.

* * * * *

UNITED STATES PATENT AND TRADEMARK OFFICE
CERTIFICATE OF CORRECTION

| | | |
|---|---|---|
| PATENT NO. | : 8,580,230 B2 | Page 1 of 1 |
| APPLICATION NO. | : 12/710633 | |
| DATED | : November 12, 2013 | |
| INVENTOR(S) | : Huang et al. | |

It is certified that error appears in the above-identified patent and that said Letters Patent is hereby corrected as shown below:

In the Specification:
In column 6, line 24

Delete "$0 \leq \times \geq 1$"

Insert --$0 \leq \times \leq 1$--
In column 8, line 22
Delete "precurs"
Insert --precursor solutions--
In column 13, line 34

Delete "$0 \leq y \geq 1$"

Insert --$0 \leq y \leq 1$--

In the Claims:
In column 16, claim 29, line 7
Delete "Fe3 + ions"
Insert --$Fe^{3+}$ ions--

Signed and Sealed this
Twenty-fifth Day of February, 2014

Michelle K. Lee
*Deputy Director of the United States Patent and Trademark Office*